United States Patent [19]

Nilsson

[11] Patent Number: 5,433,736
[45] Date of Patent: Jul. 18, 1995

[54] IMPLANTABLE MEDICAL APPARATUS AND EXTRACORPOREAL PROGRAMMING AND CONTROL UNIT THEREFOR

[75] Inventor: Kenth-Ake-Sune Nilsson, Akersberga, Sweden

[73] Assignee: Pacesetter AB, Solna, Sweden

[21] Appl. No.: 183,310

[22] Filed: Jan. 19, 1994

[30] Foreign Application Priority Data

Jan. 29, 1993 [SE] Sweden .................. 9300281

[51] Int. Cl.⁶ .............................................. A61N 1/08
[52] U.S. Cl. ......................................... 607/59; 607/30; 607/32; 607/60; 128/904
[58] Field of Search .................................. 607/30-32, 607/59-60; 128/904

[56] References Cited

U.S. PATENT DOCUMENTS 3,768,014 10/1973 Smith et al. .................. 324/158
4,614,192  9/1986 Imran et al. .................. 128/419
5,113,859  5/1992 Funke ........................... 128/419

FOREIGN PATENT DOCUMENTS 0447710  9/1991  European Pat. Off. .

Primary Examiner—William E. Kamm
Attorney, Agent, or Firm—Hill, Steadman & Simpson

[57] ABSTRACT

A system for administering medical therapy includes an implantable medical apparatus containing an audio transmitter and an audio receiver for respectively transmitting and receiving extracorporeally audible audio signals. The system also includes an extracorporeal programming and control apparatus, which also includes an audio transmitter and an audio receiver. The medical apparatus can thus communicate directly, in both directions, with the extracorporeal programming and control apparatus by means of audio signals. Such communication can take place, for example, via a telephone line, so that the patient in whom the medical apparatus is implanted need not be physically present at the location of the extracorporeal programming and control apparatus in order to establish communication.

6 Claims, 3 Drawing Sheets

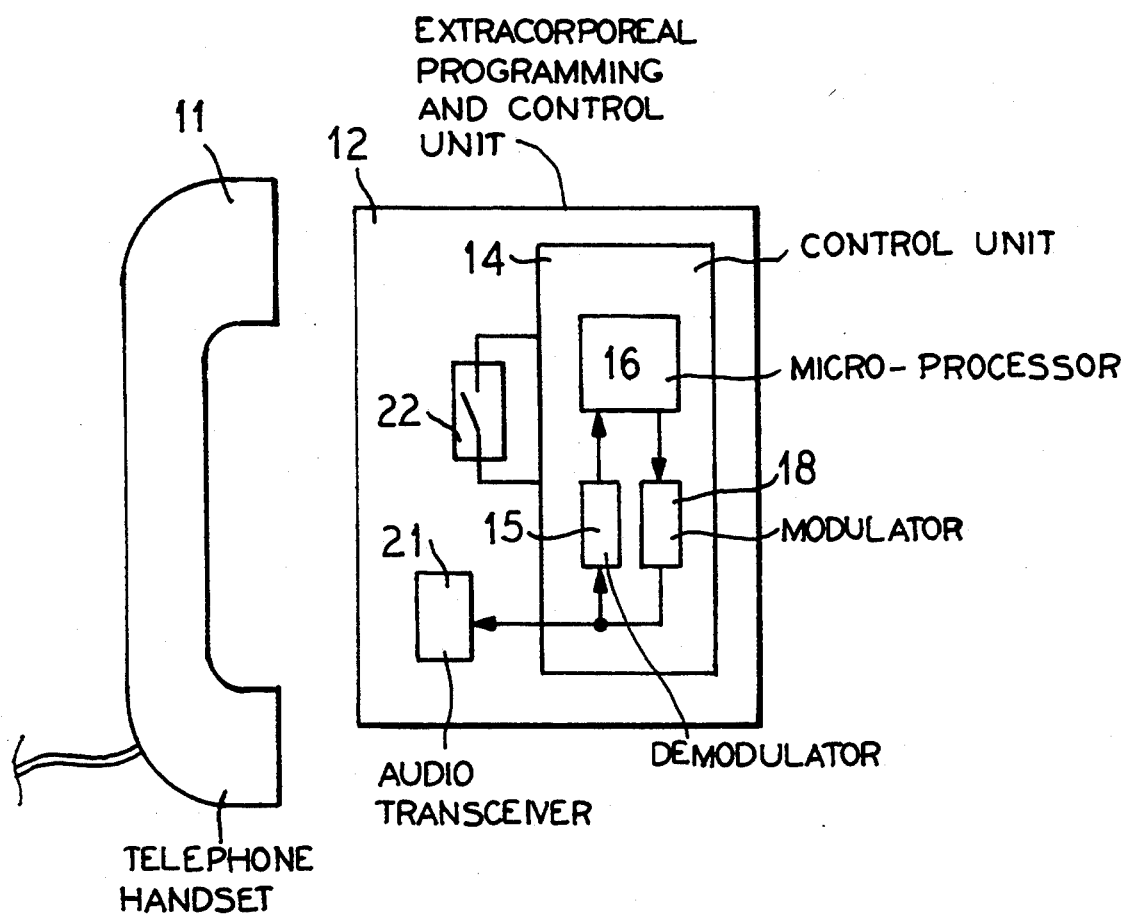

IMPLANTABLE MEDICAL APPARATUS AND EXTRACORPOREAL PROGRAMMING AND CONTROL UNIT THEREFOR

BACKGROUND OF THE INVENTION

1. Field of the Invention

The present invention relates to an implantable medical apparatus, and means for extracorporeally communicating with the medical apparatus. More specifically, the invention relates to an implantable medical apparatus having an audio transmitter for transmitting extracorporeally audible signals, and a control device for controlling the audio transmitter. The invention also relates to an extracorporeal programming and control apparatus having an audio receiver for receiving audio signals from the implantable apparatus related to a function thereof.

2. Description of the Prior Art

Patients in whom a medical apparatus, such as a pacemaker, a defibrillator or an infusion pump, is implanted must visit their physician periodically to have the function of the implantable medical apparatus checked. Such a check may disclose the need for a change in the operating mode of the device. The physician then employs a programming and control unit to retrieve information stored in the implanted device, and to send program changes to the implanted device. Information is transferred between the implanted device and the extracorporeal control device by telemetry.

Such periodic functional checks, which are usually routine and do not occasion any change in the functioning of the implanted device, can be a nuisance for the patient who must visit his or her physician for each check. This may restrict the ability of the patient, for example, to travel on extended trips.

An implantable defibrillator is disclosed in U.S. Pat. No. 4,614,192 which contains an audio transmitter which can emit audio signals indicating whether the defibrillator is active. The checking procedure begins with the placement of a magnet against the patient's skin near the defibrillator, in order to actuate a reed relay. If the defibrillator is active, a pulsed tone is emitted synchronized with heartbeats. A continuous sound signal is emitted if the defibrillator is inactive.

A pacemaker system is described in U.S. Pat. No. 3,768,014 wherein the patient carries his or her own communications unit, which is capable of receiving telemetric information from the implanted pacemaker. The communications unit has a speaker and can transmit, for example over a telephone line, information received from the pacemaker to a control apparatus. As a result, the patient does not need to visit a physician for routine checks as long as the pacemaker does not require programming. The patient must carry the communication unit on his or her person, however, in order to be able to transmit information to the physician. Additionally, the patient must remain within convenient traveling distance to the physician in the event that reprogramming should prove to be necessary.

SUMMARY OF THE INVENTION

It is an object of the present invention to provide an implantable medical apparatus which can transmit and receive information relating to its operation directly, and independently of distance, to an extracorporeal programming and control apparatus.

Another object of the present invention is to provide an extracorporeal programming and control apparatus for an implantable medical device, which is capable of transmitting and receiving information to and from an implanted medical apparatus directly and independently of distance.

The above object is achieved in an implantable medical apparatus constructed in accordance with the principles of the present invention wherein the apparatus includes an audio receiver, as well as an audio transmitter, for communicating with the extracorporeal programming and control apparatus by means of the transmission and reception of audio signals. The extracorporeal programming and control apparatus also includes both an audio transmitter and an audio receiver.

With both an audio transmitter and an audio receiver in the implantable medical device, information can be transmitted by sound waves to and from the implanted apparatus. Preferably, the audio transmitter and the audio receiver are designed to respectively transmit and receive audio signals at a frequency, or in a frequency range, suitable for transmission via a telephone line. As used herein, therefore, "audio signals" means signals having a frequency in a range from about 250 Hz to about 8,000 Hz.

In accordance with the invention, the patient no longer is restricted to the need to remain in relatively close traveling proximity to the physician and can, in principle, be located anywhere as long as the patient has access to a telephone. By telephone, the physician can then, evaluate and, if necessary, reprogram the implanted medical apparatus.

In a further embodiment of the invention, the audio transmitter and the audio receiver are combined in a single unit in the form of an audio transceiver. The use of an audio transceiver, capable of both generating and receiving audio signals, reduces the number of system components.

Preferably the control circuitry of the implanted medical apparatus includes a magnetically actuated switch, with transmission and/or reception of information being enabled when the switch is actuated (e.g. closed) by the presence of a specific magnetic field. In this embodiment, when a patient wishes to begin communication between his or her implanted medical apparatus and the physician's office, the patient need only place a magnet adjacent the implanted apparatus. The switch can be a reed relay, or some other type of component which is sensitive to a magnetic field.

In a further embodiment of the invention, the control circuitry in the implantable medical device includes a signal modulator to control the audio transmitter, so that the audio transmitter generates frequency-modulated or pulse-modulated audio signals. The implantable medical device can also include a signal demodulator so as to demodulate frequency-modulated or pulse-modulated audio signals received by the audio receiver.

Frequency modulation of the signals, i.e., changing the tone thereof, or pulse modulation of the signals, permits the transmission of a larger amount of information in a short amount of time, with only a slight risk of interference-induced information distortion.

in the extracorporeal programming and control apparatus of the invention, the acoustic transmitter therein transmits acoustic signals which can be picked-up by the acoustic receiver of the implantable medical apparatus, so that information is mutually transmittable between the implantable medical apparatus and the extracorporeal apparatus.

The extracorporeal programming and control apparatus can be devised to be capable of both transmitting and receiving audio signals, just as the implantable apparatus.

DESCRIPTION OF THE DRAWINGS

FIG. 3 shows an embodiment of the extracorporeal programming and control apparatus having a transceiver.

DESCRIPTION OF THE PREFERRED EMBODIMENTS

Figure 1:
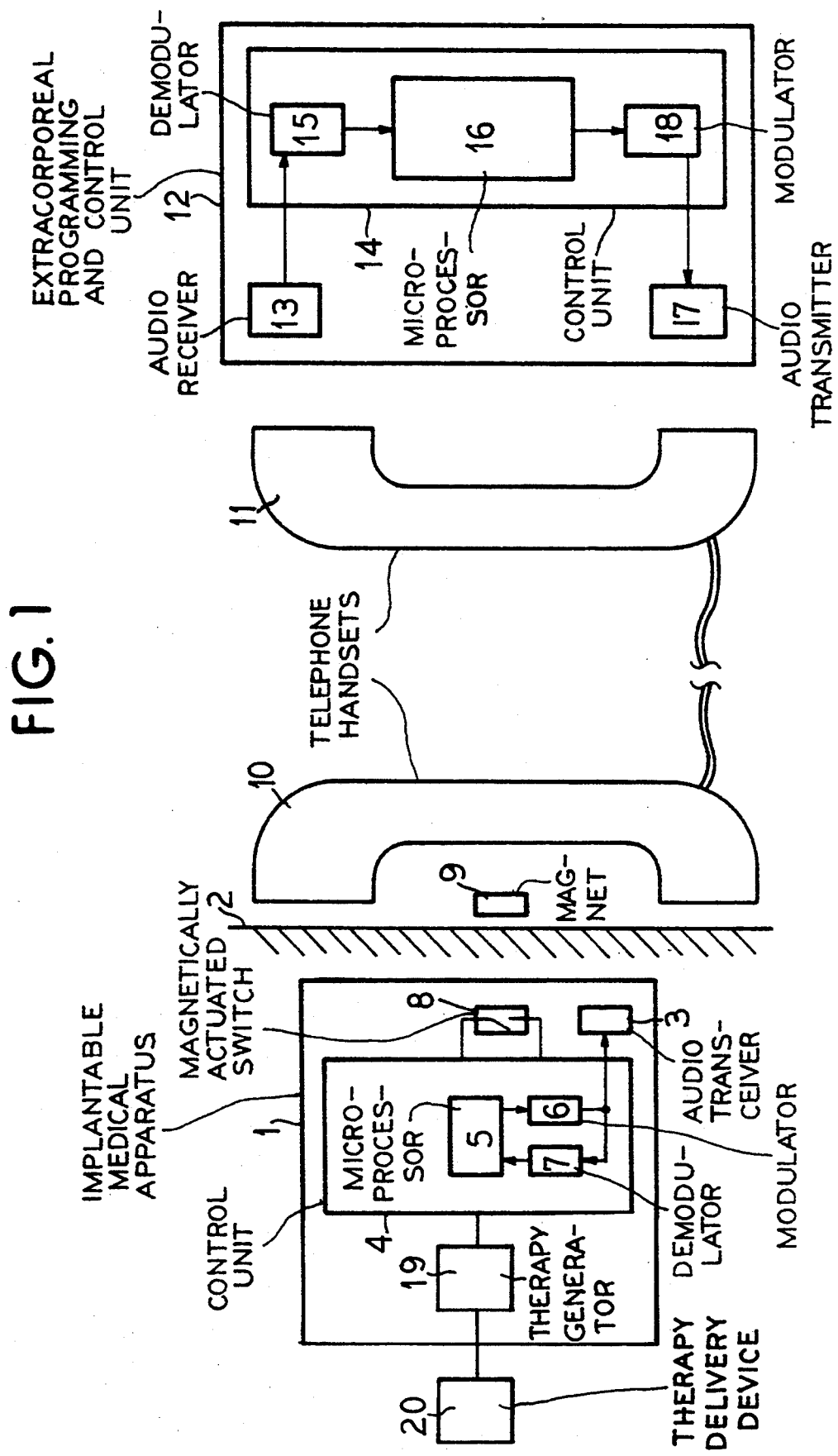
FIG. 1 shows an implantable medical apparatus and an extracorporeal programming and control apparatus, both capable of transmitting and receiving audio signals, constructed in accordance with the principles of the present invention.

The medical apparatus 1 shown in FIG. 1 is implanted beneath the skin 2 of a patient. The medical apparatus 1 may be of any type for administering therapy, such as a pacemaker, a defibrillator or an infusion device. The medical apparatus 1 includes a transceiver 3 capable of transmitting and receiving audio signals. A control unit 4 controls the operation of the medical apparatus 1 and the transceiver 3 by supplying signals to a therapy generator 19 (such as a pacing stimulation pulse generator, a defibrillation pulse generator, or a medication pump) which causes therapy (pacing, defibrillation or medication infusion) to be delivered to a patient via a therapy delivery device 20 (such as one or more pacing electrodes, a set of defibrillation electrodes, or an infusion catheter). When an audio signal containing specific data is to be generated by the transceiver 3, the data are first supplied from a microprocessor 5 in the control unit 4 to a signal modulator 6, which controls the generation by transceiver 3 of the audio signal. Audio signal received by the transceiver 3 are supplied via a signal demodulator 7 to the microprocessor 5.

The medical apparatus 1 contains a magnetically operable switch 8, for example, a reed relay or a Hall element, which is actuated (closed) in the presence of an externally applied magnetic field supplied, for example, by a permanent magnet 9. When the switch 8 is closed, the microprocessor 5 is enabled to supply data and program-related information to the transceiver 3, the signals containing the data and programming information being modulated in the modulator 6 and being emitted in the form of a modulated audio signal by the audio transceiver 3.

Figure 2:
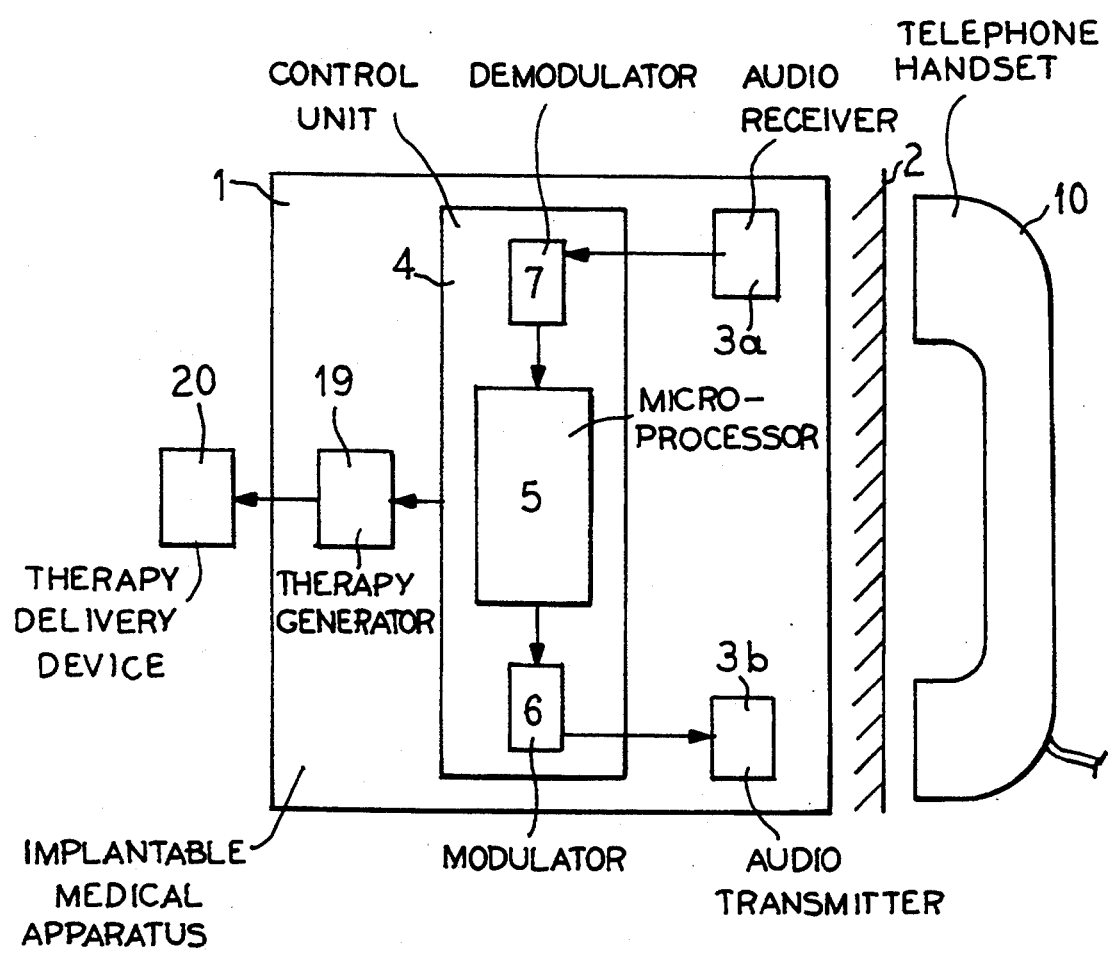
FIG. 2 shows an embodiment of the implantable medical apparatus having a separate audio transmitter and audio receiver.

The data transmitted out of the medical apparatus 1 by the transceiver 3 can be transmitted via further distances by a telephone line, for which purpose a first telephone handset 10 is placed against the body of the patient, adjacent the implanted medical apparatus 1, in order to communicate with the transceiver 3, A second telephone handset 11 is arranged to communicate with an extracorporeal programming and control apparatus 12. In the embodiment of the drawing, wherein a telephone line is employed, the programming and control apparatus 12 can be disposed at a remote location, such as a hospital or a physician's office or the like. Communication between the medical apparatus 1 and the programming and control apparatus 12, however, can also take place without the telephone link, if the programming and control device 12 is disposed sufficiently closely to, the patient so that the audio signals generated by the transceiver 3 can be picked-up by the programming and control apparatus 12. As shown in FIG. 2, a separate audio receiver 3a and an audio transmitter 3b can be used instead of the single transceiver 3. Although a magnet can again be used to place the microprocessor 5 in a transmitting mode, this is not necessary in view of the separate transmitting and receiving lines, which permit the mode of the microprocessor 5 to be set by an incoming audio signal.

For the purpose of receiving the signals generated by the transceiver 3, either via the telephone link as shown in the drawing, or by means of proximately locating the programming and control apparatus 12 relative to the patient, the programming and control apparatus 12 contains an audio receiver 13. In the embodiment shown in the drawing, the audio receiver 13 receives the audio signals via the telephone link from the transceiver 3. The data are transmitted in the programming and control apparatus 12 to a control unit 14, which contains a signal demodulator 15 which demodulates the incoming signal, and supplies the demodulated signal to a microprocessor 16. By means of a transmitter 17, the programming and control apparatus 12 can transmit data and programming instructions via the telephone line to the implanted apparatus 1, in order to change the function of the implanted apparatus 1. A signal modulator 18 modulates the signal from the microprocessor 16 which is supplied to the audio transmitter 17.

As in the implantable medical apparatus 1, the audio receiver 13 and the audio transmitter 17 can be combined in an audio transceiver 21, as shown in FIG. 3. The mode of the microprocessor 16 (transmitting or receiving) is set by a switch 22 on the control panel of the extracorporeal programming and control unit 12.

The microprocessor 16 can be provided with a program which automatically determines the most appropriate form or programming for the implanted apparatus 1 on the basis on the data received from the implanted apparatus 1, or can be used by a physician for controlling the programming of the implanted apparatus 1 with no need for the patient to come to the hospital or to the physician's office.

For the transmission of data, the audio signals which are generated are preferably frequency-modulated (in which case the modulators 6 and 18 will be standard FM modulators and the demodulators 7 and 15 will be standard FM demodulators) or pulsecode-modulated (in which case the modulators 6 and 18 will be standard PCM modulators and the demodulators 7 and 15 will be standard PCM demodulators). For example, a frequency-modulated signal can transfer analog or digital data at high speed with good insensitivity to interference.

Although modifications and changes may be suggested by those skilled in the art, it is the intention of the inventor to embody within the patent warranted hereon all changes and modifications as reasonably and properly come within the scope of his contribution to the art.

I claim as my invention:
1. A medical therapy system comprising:
    an implantable medical apparatus for administering therapy to a patient, said implantable medical apparatus including audio transmitter means for transmitting extracorporeally audible audio signals hav- ing a frequency in a range of 250 to 8,000 Hz, programmable control means for operating according to a program employing data for controlling administration of therapy to said patient and for supplying a first signal to said audio transmitter means containing information relating to said data for transmission by said audio transmitter means in said audible audio signals, and an audio receiver means connected to said control means for directly receiving extracorporeally generated audio signals also having a frequency in said range for operating said control means; and an extracorporeal programming and control apparatus including audio receiver means for receiving said audio signals from said audio transmitter means of said implantable medical apparatus, audio transmitter means for generating said extracorporeally generated audio signals receivable by said audio receiver means in said implantable medical apparatus, and control means for generating a second signal containing programming instructions and data for use by said implantable medical apparatus said audio transmitter means and said audio receiver means of said implantable medical apparatus and said audio transmitter means and said audio receiver means of said extracorporeal programming and control apparatus forming, in combination means for audibly transmitting data, in said frequency and programming instructions between said control means in said implantable medical apparatus and said control means extracorporeal programming and control apparatus.

2. A system as claimed in claim 1 wherein said audio transmitter means and said audio receiver means of said implantable medical apparatus comprise, in combination, an audio transceiver.

3. A system as claimed in claim 1 wherein said control means of said implantable medical apparatus includes a magnetically actuated switch, wherein said system comprises means for temporarily causing said switch to be disposed in a magnetic field which actuates said switch, and wherein said control means comprises means for enabling transmission of said first signal from said control means to said audio transmitter means in said implantable medical apparatus in the presence of said magnetic field.

4. A system as claimed in claim 1 wherein said implantable medical apparatus includes signal modulator means for modulating said first signal to form said audible audio signals transmitted by said audio transmitter means and a signal demodulator means for demodulating signals received by said audio receiver means in said implantable medical apparatus, and wherein said extracorporeal programming and control apparatus includes means for modulating said second signal to form said audible audio signals transmitted by said audio transmitter means in said extracorporeal programming and control apparatus and signal demodulator means for demodulating said audio signals received by said audio receiver means in said extracorporeal programming and control apparatus.

5. A system as claimed in claim 4 wherein said signal modulator means in said implantable medical apparatus and in said extracorporeal programming and control apparatus respectively comprise means for frequency-modulating said first and second signals to form frequency-modulated audible audio signals, and wherein said signal demodulator means in each of said implantable medical apparatus and said extracorporeal programming and control apparatus comprises means for demodulating said frequency-modulated audible audio signals.

6. A system as claimed in claim 4 wherein said signal modulator means in said implantable medical apparatus and in said extracorporeal programming and control apparatus respectively comprise means for pulsecode-modulating said first and second signals to form pulsecode-modulated audible audio signals, and wherein said signal demodulator means in each of said implantable medical apparatus and said extracorporeal programming and control apparatus comprises means for demodulating said pulsecode-modulated audible audio signals.

* * * * *